US009056183B2

(12) United States Patent
Deshpande

(10) Patent No.: US 9,056,183 B2
(45) Date of Patent: Jun. 16, 2015

(54) CATHETER WITH ARTICULABLE SEPTUM EXTENSION

(71) Applicant: COVIDIEN LP, Mansfield, MA (US)

(72) Inventor: Manish Deshpande, Canton, MA (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 14/085,909

(22) Filed: Nov. 21, 2013

(65) Prior Publication Data

US 2014/0081199 A1  Mar. 20, 2014

Related U.S. Application Data

(62) Division of application No. 13/248,658, filed on Sep. 29, 2011, now Pat. No. 8,636,682.

(51) Int. Cl.
*A61M 25/00* (2006.01)
*A61M 25/14* (2006.01)
*A61M 37/00* (2006.01)
(Continued)

(52) U.S. Cl.
CPC ... *A61M 25/0075* (2013.01); *A61M 2202/0413* (2013.01); *A61M 25/008* (2013.01); *A61M 1/3659* (2014.02); *A61M 2025/0037* (2013.01); *A61M 1/3653* (2013.01); *A61M 25/003* (2013.01); *A61M 25/007* (2013.01); *A61M 25/0074* (2013.01); *A61M 2025/0031* (2013.01); *A61M 2025/0073* (2013.01); *A61M 1/285* (2013.01); *A61M 1/3661* (2014.02)

(58) Field of Classification Search
CPC ............ A61M 1/3653; A61M 25/003; A61M 1/3661; A61M 25/0075; A61M 25/007; A61M 25/0074; A61M 2025/0031; A61M 2025/0073; A61M 1/285; A61M 2025/0037; A61M 25/008; A61M 2202/0413; A61M 1/3659; A61M 2025/0074; A61M 2025/0075
See application file for complete search history.

(56) References Cited

U.S. PATENT DOCUMENTS 5,112,301 A   5/1992   Fenton, Jr. et al.
5,156,600 A   10/1992  Young
(Continued)

FOREIGN PATENT DOCUMENTS

EP   2119468 A1   11/2009
EP   2168625 A1   3/2010
(Continued)

OTHER PUBLICATIONS

European Search Report from EP 12 18 3701 mailed Dec. 4, 2012.
(Continued)

*Primary Examiner* — Adam Marcetich
(74) *Attorney, Agent, or Firm* — John Paul Mello, Esq.

(57) ABSTRACT

A catheter includes an elongated tubular body including a first wall and second wall defining first and second lumens, respectively. Each wall extends to a distal end and defines a distal opening. The first and second walls may each include one or more side openings disposed proximal of the distal end. The first and second lumens are separated by a septum. The septum includes a septum extension extending distally from the septum. The septum extension is adapted to articulate relative to the septum in response to fluid flow into and out of the distal openings of the first and second lumens. The septum extension is dimensioned to partially obstruct fluid flow into the catheter through one of the distal openings upon the articulation of the septum extension.

15 Claims, 2 Drawing Sheets

(51) Int. Cl.
*A61M 39/00* (2006.01)
*A61M 39/22* (2006.01)
*A61M 1/36* (2006.01)
*A61M 1/28* (2006.01)

(56) References Cited

U.S. PATENT DOCUMENTS

| | | |
|---|---|---|
| 5,165,450 A | 11/1992 | Marrelli |
| 5,224,938 A | 7/1993 | Fenton, Jr. |
| 5,569,182 A | 10/1996 | Twardowski et al. |
| 5,685,867 A | 11/1997 | Twardowski et al. |
| 5,807,349 A | 9/1998 | Person et al. |
| 6,004,395 A | 12/1999 | Yim et al. |
| 6,056,001 A | 5/2000 | Boyles et al. |
| 6,098,661 A | 8/2000 | Yim et al. |
| 6,293,958 B1 | 9/2001 | Berry et al. |
| 7,090,654 B2 | 8/2006 | Lotito et al. |
| 7,776,005 B2 | 8/2010 | Haggstrom et al. |
| 8,636,682 B2 | 1/2014 | Deshpande |
| 2001/0047834 A1 | 12/2001 | Menin et al. |
| 2002/0156430 A1 | 10/2002 | Haarala et al. |
| 2002/0165492 A1 | 11/2002 | Davey et al. |
| 2005/0033264 A1 | 2/2005 | Redinger |
| 2006/0253063 A1 | 11/2006 | Schweikert |
| 2008/0097350 A1 | 4/2008 | Bell et al. |
| 2009/0054874 A1 | 2/2009 | Barron et al. |
| 2009/0093748 A1 | 4/2009 | Patterson et al. |
| 2009/0187141 A1 | 7/2009 | Lareau et al. |
| 2009/0216174 A1 | 8/2009 | Nardeo |
| 2010/0081986 A1 | 4/2010 | Matson et al. |
| 2011/0263976 A1 | 10/2011 | Hassan et al. |

FOREIGN PATENT DOCUMENTS

| | | |
|---|---|---|
| WO | 2004096334 A1 | 11/2004 |
| WO | 2006002192 A2 | 1/2006 |
| WO | 2007111874 A2 | 10/2007 |
| WO | 2010102817 A1 | 9/2010 |

OTHER PUBLICATIONS

Australian Examiner's Report from Australian Appln. No. 2012216812 dated Feb. 22, 2013.

First Office Action issued in Chinese Appl. No. 201210059962.5 dated Apr. 26, 2013.

Office Action issued in the corresponding Japanese Application No. 2012-211179 dated Sep. 5, 2013.

CATHETER WITH ARTICULABLE SEPTUM EXTENSION

CROSS-REFERENCE TO RELATED APPLICATIONS

This application is a divisional of U.S. patent application Ser. No. 13/248,658, filed on Sep. 29, 2011, the entire contents of which are hereby incorporated by reference.

BACKGROUND

1. Technical Field

The present disclosure relates generally to medical catheters, and more particularly to a multiple lumen catheter having an articulable septum extension.

2. Description of the Related Art

Catheters are flexible medical instruments for use in the introduction and withdrawal of fluids to and from body cavities, ducts and vessels. Catheters are used for many different applications within the human body including the administration of liquid therapeutic agents and the removal of bodily fluids for testing, monitoring, or disposal. Catheters have a particular application in hemodialysis procedures, in which blood is withdrawn from a blood vessel, directed to a hemodialysis unit for dialysis or purification, and subsequently returned to the blood vessel.

Typically, dialysis catheters define at least two lumens including a venous lumen and an arterial lumen. The arterial lumen withdraws blood from the patient and delivers the blood to a dialyzer. The venous lumen receives purified blood from the dialyzer and returns the blood to the patient. The venous and arterial lumens may include distal openings adjacent the tip of the catheter. In addition, the venous and arterial lumens may also include side openings which provide redundant or alternate flow paths to and from the arterial and venous lumens.

The efficiency of a hemodialysis procedure may be reduced by recirculation of blood flow at a distal end of the catheter. Recirculation occurs when dialyzed blood exiting the venous lumen is drawn directly back into the arterial lumen of the catheter. To overcome this drawback, some catheter devices stagger the openings of the catheter lumens such that the opening of the venous lumen is disposed distally beyond the opening of the arterial lumen. These catheter devices, however, also suffer from various additional drawbacks. For example, the staggered openings of the venous lumen and arterial lumen render the catheter less suitable for reversing fluid flow through the catheter. Reversibility of fluid flow through the catheter may be used to remove the formation of thrombus within an opening of the catheter. Thus, the staggered openings may disadvantageously indirectly result in a higher likelihood of flow occlusion within the catheter.

Therefore, it would be desirable to overcome the disadvantages and drawbacks of the prior art with a multiple lumen catheter minimizes the likelihood of recirculation without negatively affecting the ability of the catheter to eliminate thrombus formation. It would also be highly desirable if the catheter and its constituent parts are easily and efficiently manufactured and assembled.

SUMMARY

Accordingly, the present disclosure is directed to a catheter having an elongated tubular body including a first wall and second wall defining first and second lumens, respectively. The elongated tubular body defines a longitudinal axis. Each wall extends to a distal end and defines a distal opening. One of the first and second lumens permits fluid inflow at the distal opening of the respective one of the first and second lumens and the other of the first and second lumens permits fluid outflow at the distal opening of the respective one of the first and second lumens.

The first and second walls may each include one or more side openings disposed proximal of the distal end. The first and second lumens are separated by a septum that extends to the distal end of the catheter. The septum includes a septum extension extending distally from the septum. The septum extension is adapted to articulate about a distal end of the septum at an acute angle relative to the longitudinal axis. The septum and the septum extension may be integrally formed.

In embodiments, the septum extension is cantilevered to the septum. The septum extension is adapted to articulate relative to the septum in response to fluid flow to and from the distal opening of the first and second lumens. The septum extension is dimensioned to partially obstruct fluid flow into the catheter through one of the distal openings upon the articulation of the septum extension.

In certain embodiments, the septum extension includes a base and a body. The base defines two or more recesses that permit the body of the septum extension to articulate towards one of the first and second lumens while fluid is flowing to and from the distal openings of the first and second lumens. The septum extension is articulable in a first direction towards one of the first and second lumens. The septum extension is articulable in a second direction towards the other of the first and second lumens when fluid flow is reversed.

In other embodiments, the septum extension may include a first thickness and a second thickness different from the first thickness. One of the first and second thicknesses facilitates the movement of the septum extension relative to the septum. The septum extension includes one or more recesses that permit the septum extension to articulate relative to the septum.

In some embodiments, the septum extension includes structure to further enhance movement of the septum extension. The septum extension may include a protuberant distal end. The protuberant distal end may include one or more of a curvilinear configuration, a spherical configuration, or a polygonal configuration.

The septum defines a plane. The first and second wall are substantially symmetrically disposed about the plane.

According to one aspect, the present disclosure is directed to a method of limiting undesirable recirculation in a catheter. The method involves providing a catheter having a tubular body defining a pair of side openings, an arterial lumen, and a venous lumen, the arterial lumen and the venous lumen being separated by a septum, the septum including an articulable septum extension. The method includes the step of articulating the septum extension relative to the septum to restrict fluid flow into the distal opening of the arterial lumen.

BRIEF DESCRIPTION OF THE DRAWINGS

The objects and features of the present disclosure, which are believed to be novel, are set forth with particularity in the appended claims. The present disclosure, both as to its organization and manner of operation, together with further objectives and advantages, may be best understood by reference to the following description, taken in connection with the accompanying drawings, as set forth below.

DETAILED DESCRIPTION OF THE EXEMPLARY EMBODIMENTS

The exemplary embodiments of the catheter and methods of use disclosed are discussed in terms of medical catheters for the administration of fluids (withdrawal, introduction, etc.) to/from the body of a subject and more particularly, in terms of a catheter including a catheter tip that limits undesirable recirculation during use to facilitate unobstructed fluid flow to/from the catheter. The catheter is advantageously configured to facilitate reversible fluid flow between lumens thereof. The present disclosure may be employed with a range of catheters, such as, for example, hemodialysis, peritoneal, infusion, PICC, CVC, and port for a variety of catheter applications including surgical, diagnostic and related treatments of diseases and body ailments of a subject.

In the discussion that follows, the term "proximal" will refer to the portion of a structure that is closer to a practitioner, while the term "distal" will refer to the portion that is further from the practitioner. According to the present disclosure, the term "practitioner" refers to a doctor, nurse or other care provider and may include support personnel. As used herein, the term "subject" refers to a human patient or other animal.

The following discussion includes a description of a catheter in accordance with the principles of the present disclosure. Reference will now be made in detail to the exemplary embodiments of the disclosure, which are illustrated in the accompanying figures.

Figure 1:
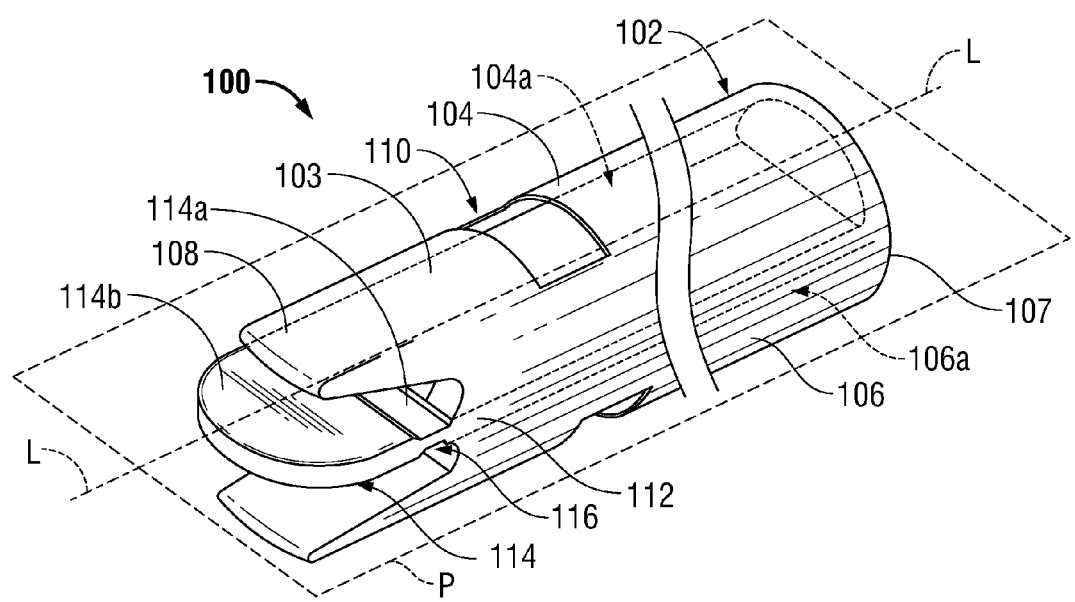
FIG. 1 is a perspective view of a distal end of one embodiment of a presently disclosed catheter in accordance with the principles of the present disclosure in a non-flow or static state.

In the figures, like components are designated by like reference numerals throughout the several views. Referring initially to FIG. 1, the present disclosure, according to one embodiment, is directed to a catheter 100.

Catheter 100 has an elongated tubular body 102 defining a longitudinal axis "L." Body 102 has a cylindrical outer surface 103 that may be variously dimensioned and attachable to other medical devices. As appreciated, outer surface 103 may have various cross-sectional configurations, such as, for example, oval, rectangular, elliptical, and polygonal.

Elongated tubular body 102 includes a first wall 104 and second wall 106. First wall 104 defines a first lumen 104a and second wall 106 defines a second lumen 106a. The lumens 104a, 106a extend along a length or a portion of the length of the tubular body 102 to distal openings 118. Although first and second lumens 104a, 106a and distal openings 118 are illustrated to have a D-shaped configuration, any other suitable configuration is envisioned, such as oval, rectangular, elliptical, and polygonal.

Lumens 104a, 106a may be uniformly dimensioned or include alternative dimensional cross sections within body 102, such as, narrow and broad portions, converging surfaces, or undulating surfaces, according to the particular flow indications and/or flow rate requirements. Suitably, first lumen 104a and second lumen 106a may extend to alternative lengths. According to embodiments, body 102 may include any number of lumens such as a triple lumen configuration.

Each wall 104, 106 extends from a proximal end 107 to a distal end 108 and may define one or more side openings 110 disposed proximal of distal end 108. As illustrated in FIG. 1, each wall 104, 106 may include extensions that extend beyond the first and second lumens 104a, 106a. In embodiments, each wall 104, 106 may extend only to the distal openings 118 of one of the respective first and second lumens 104a, 106a. The one or more side openings 110 may be disposed on any suitable portion of elongated tubular body 102. In particular, the one or more side openings 110 may be disposed in the outer surface 103 and may be positioned anywhere along the circumference of the body 102 proximal to the distal end 108 of the tubular body 102. The side openings 110 may be any suitable size and/or have any suitable geometry. The side openings 110 may also have contoured edges formed or may be otherwise smoothed to minimize the likelihood of thrombus formation.

Figure 2:
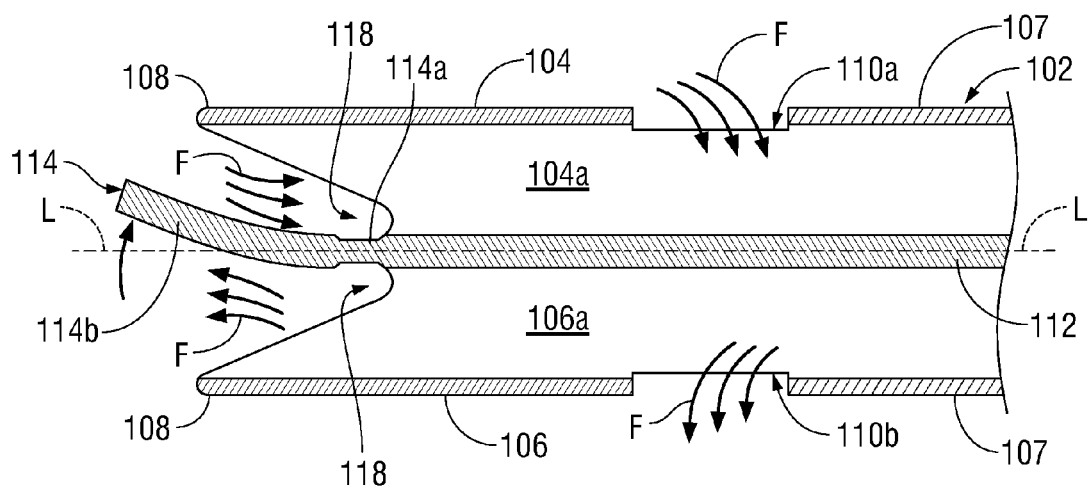
FIG. 2 is a cross-sectional view of the distal end of the presently disclosed catheter in a fluid flow state.

As best depicted in FIG. 2, first wall 104 may include a first side opening 110a in fluid communication with first lumen 104a and second wall 106 may include a second side opening 110b in fluid communication with second lumen 106a. Either the first lumen 104a or the second lumen 106a may function as a venous lumen or an arterial lumen of the catheter 100. Typically, the arterial lumen is used to withdraw blood from the patient (e.g., via suction) and direct the blood to a dialyzer, while the venous lumen is used to return dialyzed blood to the patient from the dialyzer. The catheter 100 may be configured for reversible flow to wash away thrombus or other undesirable debris which may build up on the catheter 100. As used herein, "configured for reversible flow" means that the catheter is configured such that either lumen 104a and 106a may function as the arterial or venous lumen with no appreciable change to the flow characteristics of the catheter. The venous and arterial lumens are separated by a septum 112 which defines a plane "P." Septum 112 is medially disposed, along a substantial portion of the longitudinal length of body 102, between first lumen 104a and second lumen 106a.

First and second walls 104, 106 may be substantially symmetrically disposed about plane "P." The arterial lumen permits fluid inflow at distal end 108 adjacent respective first or second wall 104, 106. The venous lumen permits fluid outflow at distal end 108 adjacent the other respective first or second wall 104, 106.

Septum 112 includes a septum extension 114 extending distally from septum 112. Septum extension 114 is movable relative to septum 112 in response to fluid flow through first and second lumens 104a, 106a in order to limit undesirable recirculation of fluid "F" through the arterial lumen of the catheter 100. Movement of the septum extension 114 occurs in response to fluid flow through the catheter 100. More specifically, a pressure difference is created between opposing surfaces of septum extension 114 as fluid flows into and out of distal openings 118. This pressure differential induces a net force from the fluid outflow side (i.e., venous lumen) to the fluid inflow side (i.e., arterial lumen), causing septum extension 114 to articulate, pivot, or deflect towards the fluid inflow side.

Most notably, septum extension 114 is movable towards the arterial lumen in response to fluid flow through catheter 100. For example, when fluid "F" is flowing into first lumen 104a and out of second lumen 106a, septum extension 114 will articulate towards first lumen 104a as shown in FIG. 2. Alternatively, if the direction of flow is reversed such that fluid "F" flows out from first lumen 104a and into second lumen 106a, septum extension 114 will articulate about longitudinal axis "L" toward second lumen 106a and second wall 106 in the same manner as described above with respect to the opposite fluid flow direction.

Septum extension 114 may be cantilevered to septum 112 to form a hinge relative to septum 112 and includes a base 114a and a septum body 114b. In one embodiment, base 114a of septum extension 114 includes a first reduced thickness to facilitate articulation of body 114b about base 114a in response to a predetermined fluid flow rate through catheter 100 sufficient to achieve the pressure differential discussed above. The reduced thickness of base 114a may be effected by providing one or more recesses 116 on one or both sides of septum extension 114 that permit septum extension 114 to bend, deflect or articulate relative to septum 112. Alternately, base 114a may be formed of a different material than septum body 114b to facilitate articulation of septum body 114b in relation to septum 112 about base 114a. The material of base 114a may be any suitable flexible material. The materials of the presently disclosed catheters will be discussed in greater detail below.

Two or more recesses 116 may be symmetrically disposed relative to each other to define base 114a of septum extension 114 and to permit septum body 114b of septum extension 114 to articulate while fluid is flowing through first and second lumens 104a, 106a. As appreciated, septum extension 114 may be articulable about a distal end of septum 112 at an acute angle relative to longitudinal axis "L." In addition, septum 112 and septum extension 114 may be integrally formed or separately connected.

Movement of septum extension 114 towards the arterial or inflow lumen increases inflow resistance at the distal end 108 of catheter 100 to limit undesirable recirculation. In this respect, as septum extension 114 articulates or bends toward the distal opening 118 of the arterial lumen relative to septum 112, distal opening 118 of the arterial lumen is at least partially obstructed by septum extension 114. This obstruction restricts fluid inflow through distal opening 118. Conversely, fluid outflow from distal opening 118 of the venous lumen is unrestricted. Thus, the primary fluid flow into the arterial lumen will be through the side opening 110 and the primary fluid from the venous lumen will be from the distal opening 118 of the venous lumen. Since the distal openings 118 and side openings 110 are spaced, the likelihood for recirculation to occur is minimized.

Figure 3:
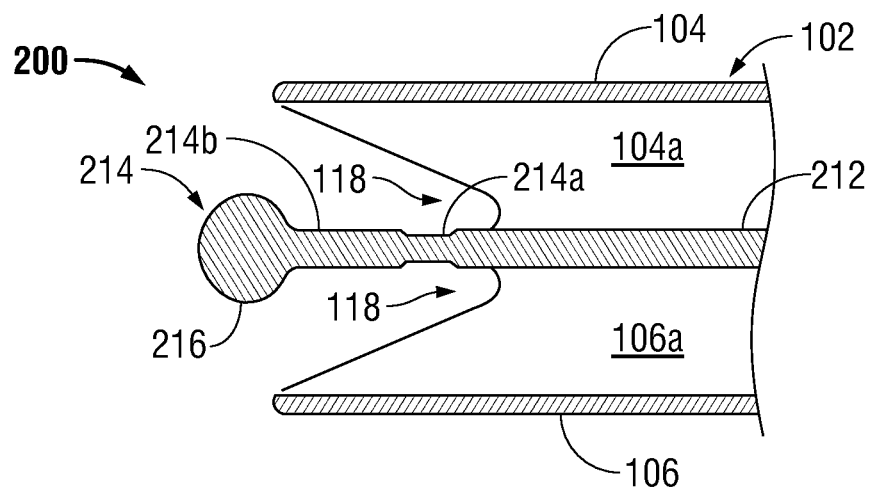
FIG. 3 is a cross-sectional view of a distal end of another embodiment of the presently disclosed catheter in accordance with the principles of the present disclosure in a non-flow or static state.

As shown in FIG. 3, another embodiment of the presently disclosed catheter is generally referred to as catheter 200. Catheter 200 is similar to catheter 100 and is described herein only to the extent necessary to describe the differences in construction and operation. Catheter 200 has an elongated tubular body 102 that includes first wall 104 and second wall 106. First wall 104 defines a first lumen 104a and second wall 106 defines a second lumen 106a. The lumens 104a, 106a extend along a length or a portion of the length of the tubular body 102 to distal openings 118. Either the first lumen 104a or the second lumen 106a may function as a venous lumen or an arterial lumen as discussed above with regard to catheter 100. The venous and arterial lumens are separated by a septum 212 that is medially disposed, along a substantial portion of the longitudinal length of body 102, between first lumen 104a and second lumen 106a.

Septum 212 includes a septum extension 214 extending distally from septum 112. Septum extension 214 includes a base 214a and a septum body 214b. A portion of septum body 214b has enlarged dimensions to further enhance pivotal or articulating movement of the septum extension 214. For example, as depicted in FIG. 3, septum body 214b includes a protuberant distal end 216 that further enhances pivotal or articulating movement of the septum body 214b relative to base 214a in response to a predetermined fluid flow rate through catheter 200 sufficient to achieve the pressure differential discussed above with respect to catheter 100. As can be appreciated, protuberant distal end 216 may have any suitable shape sufficient to enhance pivotal or articulating movement of the septum body 214b. For example, protuberant distal end 216 may have a curvilinear configuration, a spherical configuration, or a polygonal configuration.

Any of the presently disclosed surfaces and/or components of the presently disclosed catheters may be planar or non-planar, such as, for example, arcuate, undulating, or textured.

The components of the presently disclosed catheters are fabricated from materials suitable for medical applications, such as, for example, polymerics or metals, such as stainless steel, depending on the particular catheter application and/or preference of a practitioner. Semi-rigid and rigid polymerics are contemplated for fabrication, as well as resilient materials, such as molded medical grade polypropylene or polyurethane. One skilled in the art, however, will realize that other materials and fabrication methods suitable for assembly and manufacture, in accordance with the present disclosure, also would be appropriate.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A catheter comprising:
    an elongated tubular body including a first wall and second wall defining first and second lumens, respectively, each wall extending to a distal end and defining a distal opening, the first and second lumens being separated by a septum, the septum including a septum extension extending distally from the septum, the septum extension being adapted to articulate relative to the septum in response to fluid flow into and out of the distal openings of the first and second lumens, wherein the septum extension is dimensioned to partially obstruct fluid flow into the catheter through one of the distal openings upon the articulation of the septum extension.

2. The catheter of claim 1, wherein the septum extension is cantilevered to the septum.

3. The catheter of claim 1, wherein the septum extension includes a first thickness and a second thickness different from the first thickness, one of the first and second thicknesses facilitating the movement of the septum extension relative to the septum.

4. The catheter of claim 1, wherein the septum extension includes at least one recess that permits the septum extension to articulate relative to the septum.

5. The catheter of claim 4, wherein the septum extension includes a base and a body, the base defining at least two recesses that are symmetrically disposed relative to each other to permit the body of the septum extension to articulate towards one of the first and second lumens while fluid is flowing to and from the distal openings of the first and second lumens.

6. The catheter of claim 5, wherein the septum extension is articulable in a first direction towards one of the first and second lumens, the septum extension being articulable in a second direction towards the other of the first and second lumens when fluid flow is reversed.

7. The catheter of claim 1, wherein the septum and the septum extension are integrally formed.

8. The catheter of claim 1, wherein one of the first and second lumens permits fluid inflow at the distal opening of the respective one of the first and second lumens and the other of the first and second lumens permits fluid outflow at the distal opening of the respective one of the first and second lumens.

9. The catheter of claim 1, wherein the septum defines a plane, the first and second walls being substantially symmetrically disposed about the plane.

10. The catheter of claim 1, wherein the septum extension includes a protuberant distal end.

11. The catheter of claim 10, wherein the protuberant distal end includes at least one curvilinear configuration, a spherical configuration, or a polygonal configuration.

12. The catheter of claim 1, wherein the elongated tubular body defines a longitudinal axis and the septum extension is articulable about a distal end of the septum at an acute angle relative to the longitudinal axis.

13. A catheter comprising:

an elongated tubular body;

a septum disposed in the elongated tubular body, the septum and the elongated tubular body defining first and second lumens terminating at respective first and second distal openings; and a septum extension extending distally from the septum, the septum extension articulable relative to the septum in response to fluid flow into and out of the first and second distal openings, wherein the septum extension is dimensioned to partially obstruct fluid flow into the catheter through one of the distal openings upon the articulation of the septum extension.

14. The catheter of claim 13, wherein one of the first and second lumens permits fluid inflow at the distal opening of the respective one of the first and second lumens and the other of the first and second lumens permits fluid outflow at the distal opening of the respective one of the first and second lumens.

15. The catheter of claim 13, wherein the elongated tubular body includes a first wall and second wall defining the first and second lumens, respectively, and wherein the septum defines a plane, the first and second wall being substantially symmetrically disposed about the plane.

* * * * *